United States Patent

Waggener

[11] Patent Number: 5,879,407
[45] Date of Patent: Mar. 9, 1999

[54] WEAR RESISTANT BALL AND SOCKET JOINT

[76] Inventor: Herbert A. Waggener, 7282 178th St., Chippewa Falls, Wis. 54729

[21] Appl. No.: 895,747

[22] Filed: Jul. 17, 1997

[51] Int. Cl.[6] ........................................... A61F 2/32
[52] U.S. Cl. ............................................... 623/22
[58] Field of Search .................. 623/16, 18, 21, 623/22, 23, 20

[56] References Cited

U.S. PATENT DOCUMENTS

| | | | |
|---|---|---|---|
| Re. 32,449 | 6/1987 | Claussen et al. | 623/22 X |
| 5,133,754 | 7/1992 | Laghi . | |
| 5,152,794 | 10/1992 | Davidson | 123/18 X |
| 5,180,394 | 1/1993 | Davidson | 623/23 X |
| 5,181,929 | 1/1993 | Prats et al. | 623/23 |
| 5,217,499 | 6/1993 | Shelley | 623/22 |
| 5,326,362 | 7/1994 | Shetty et al. | 623/66 |
| 5,336,266 | 8/1994 | Caspari et al. | 623/20 |
| 5,370,694 | 12/1994 | Davidson | 623/18 X |
| 5,376,125 | 12/1994 | Winkler | 623/23 |
| 5,425,779 | 6/1995 | Schlosser et al. | 623/23 |
| 5,593,452 | 1/1997 | Higham et al. | 623/23 |
| 5,645,601 | 7/1997 | Pope et al. | 623/22 X |
| 5,702,448 | 12/1997 | Buichel et al. | 623/23 X |

FOREIGN PATENT DOCUMENTS 0 461 019  12/1991  European Pat. Off. ................. 623/22

*Primary Examiner*—Michael J. Milano
*Attorney, Agent, or Firm*—Terrance L. Siemens

[57] ABSTRACT

A ball and socket joint providing longevity especially suitable for use in implants in human bodies. The ball is designed to incorporate specified strength, hardness, and smoothness characteristics. The socket has a cooperating bearing surface which is less hard than that of the ball. This combination of characteristics lead to maximal mutual bearing contact which minimizes local friction and abrasion. Both components are biologically inert. One component is hydrophilic. The ball is preferably formed from a ceramic, such as a metal or silicon oxide or carbide. The socket preferably has a noble metal alloy liner partially surrounding the ball. The socket further includes an insulator isolating the liner from the socket structural member, should the latter be formed from a different metal. The liner can be formed in complementary segments to avoid fracture or splitting. The liner is either mechanically entrapped by the socket structural member or is adhered thereto. The novel ball and socket joint minimizes wear and chemical, electrochemical, and mechanical deterioration in the environment of the human body.

10 Claims, 2 Drawing Sheets

WEAR RESISTANT BALL AND SOCKET JOINT

BACKGROUND OF THE INVENTION

1. FIELD OF THE INVENTION

The present invention relates to a ball and socket joint particularly suitable for a prosthesis. More specifically, construction of the joint includes a relatively pliant socket material, while the ball has a hard, rigid surface. Unlike many prior art joints employing polymer liners, the relatively pliant material is selected from a material which is usually categorized as hard, such as metals. The benefit obtained by relative compliance is that when forces are imposed urging the ball against the socket, one contact surface yields and conforms to the other contact surface. Mutual contact area is thereby maximized, thus reducing maximal loading at any one localized point. When maximal localized loads are minimized, wear is mitigated.

A crucial combination of characteristics of the respective materials include specified values of surface hardness, tensile strength, smoothness, and breaking stress. Materials forming the contact surfaces are selected to further include biocompatibility, lack of cold flow, and susceptibility to advantageous forming techniques such as isostatic forming, rolling, and machining.

2. DESCRIPTION OF THE PRIOR ART

Prosthetic ball and socket joints are called upon to provide many qualities rendering them durable and suitable for their biological environments. Consequently, they are fabricated to precise dimensions from exotic, expensive materials. Also, they are implanted within a person in a demanding surgical operation, which also is expensive. Therefore, it is expensive and undesirable to require a replacement procedure in the lifetime of the patient. It follows that it is imperative that the joint last as long as is feasible.

Wear is a consideration in longevity of the ball and socket joint. Wear can modify the relative positions of the ball and socket, and can also release or generate debris in the form of particles, which can interfere with various body functions. Either of these two conditions may require that the joint be replaced with a new joint.

Another important consideration is that of progressive chemical deterioration of a component of the joint, particularly where mechanical removal of chemically formed films is a possibility. Chemical deterioration can lead to degradation of the smoothness of one surface or another. This has unfavorable implications for friction and consequent generation of localized heat and also for abrasion. Both localized heat and abrasion can reduce longevity of the implanted joint.

The wear aspect of joint operation has generally been addressed in the prior art by maximizing smoothness and hardness of the contact surfaces of the ball and socket members. An example is seen in U.S. Pat. No. 5,152,794, issued to James A. Davidson on Oct. 6, 1992. Davidson teaches coating of prosthetic surfaces with zirconium nitride and oxide. Unlike the device of Davidson, the present invention sets forth certain critical characteristics of materials selected for ball and socket components, and also specified quantitative values for these characteristics. U.S. Pat. No. 5,370,694, issued to James A. Davidson on Dec. 6, 1994, also discusses zirconium oxide and nitride, but sheds little if any further light on the novel parameters.

A method resulting in a titanium nitride surface of improved hardness and reduced friction is shown in U.S. Pat. No. 5,326,362, issued to H. Ravindranath Shetty et al. on Jul. 5, 1994. As in the case of Davidson, Shetty et al. is silent regarding the role of the combination of novel combination of characteristics, and upon the specified quantitative values thereof which form the thrust of the present invention.

A resilient member lining a rigid socket is shown in U.S. Pat. No. 5,425,779, issued to Marc H. Schlosser et al. on Jun. 20, 1995. However, unlike the present invention, the lining member is preferably made from ultra high molecular weight polyethylene (UHMWPE). Deficiencies of UHMWPE are noted in Davidson '794, and include, among other characteristics, creepage upon heating. By contrast, the resilient lining member of the present invention is made from a material not susceptible to creepage or flow.

U.S. Pat. No. 5,217,499, issued to Philp Shelley on Jun. 8, 1993, describes the socket of a ball and socket joint which has screw holes penetrating the socket member. However, Shelley fails to discuss the novel combination of characteristics, including the specified quantitive values thereof.

None of the above inventions and patents, taken either singly or in combination, is seen to describe the instant invention as claimed.

SUMMARY OF THE INVENTION

The present invention improves upon prior art ball and socket joint prostheses by reducing maximal localized frictional forces generated between ball and socket members. This is accomplished by providing a liner within the socket and a ball, both of which are of specified smoothness, hardness, and elasticity characteristics, and are chemically inert within the environment of the body.

Hardness of the two elements is not equal. As a normal force urging the ball against the socket increases, the liner of the socket tends to respond by conforming or by grossly yielding. The socket surface tends to conform to the ball. If the overall or large order shape of the ball and socket are nearly equal, the small deformation spreads the applied load over maximal surface area. Wear occurs primarily upon relative lateral motion of the ball and socket under normal load. At the outset of lateral motion between the ball and socket, localized stresses arise between adjacent asperities existing on each of the two surfaces. Gross lateral motion can occur either by climbing or sliding of the asperities over or past each other, or by localized microfracture failures occurring in the weaker of the two materials. The smoothness of the harder material, together with the strength of the weaker materials, permits the climbing or sliding mechanism to dominate over the fracture failure mechanism. Maximal localized loading on the socket surface is minimized, and consequent mechanical abrasion and friction between ball and socket are correspndingly minimized.

Also, hardnesses of materials of the socket liner and of the ball are specified to be of a value greater than that of body tissue materials. This will prevent a solid particle of body tissue from abrading either ball or socket. The body tissue particle eventually migrates to the periphery of the liner, and is expelled.

Smoothness is another important characteristic, which reduces surface deterioration, friction and heat, as discussed above and in the prior art. Certain values for requisite smoothness are set forth hereinafter.

In summary, the most important relative properties are such that the ball is quite hard and quite smooth. The liner is less hard than the ball and is relatively elastic.

Materials for achieving the desired characteristics of contact surfaces of the ball and socket are also selected and fabricated to exhibit lack of chemical activity in a body environment. This prevents slow but progressive deterioration of surfaces of the joint components that would release potentially reactive particles into the body, and which would erode the components over time. Chemical-mechanical erosion is thus eliminated.

In a further improvement, it is desired to form the ball monolithically from a material suitable for the surface of the ball. This parameter of the invention both eliminates a manufacturing step found in prior art fabrication techniques, and also assures that no coating will degrade and thus expose a different material which could result in particle release and accelerated wear of the ball or socket. Ball and socket materials must further not be subject to deformation by spontaneously flowing or creeping.

The ball must be fabricated from a material which can be shaped and smoothed by economical methods, and still be machinable. Smoothing, or micropolishing, of a spherical configuration is economically achieved in known manner, such as by exposing the ball to high isostatic pressure, or by rolling the subject spherical object under pressure between opposed moving surfaces. These methods have been widely employed in the manufacture of ball bearings. The material selected for the ball must be susceptible to this treatment and also to machining so that a shank can be connected for attachment to a patient's bone. This is so because to introduce a bore into the ball prior to forming the spherical shape and performing micropolishing would potentially distort the ball from its ideal configuration. Therefore, the sphere is formed prior to forming a bore for accepting a shank.

After the smoothing operation, the ball must be machined or otherwise shaped to accept a shank or similar structure for attachment to a body part. This requirement eliminates many materials from consideration due to the sequence of operations in formation of a suitable ball. In order to exploit known methods and equipment employed in the smoothing step as performed by rolling between opposing surfaces, the subject object must retain a spherical configuration until smoothing is completed. The spherical object must then have a hole drilled or machined therein for accepting the shank. Reversing these steps will cause rolling to deform or break the spherical object. Therefore, the sequence of operation is predetermined, and a suitable material must be employed which allows machining, either by conventional rotary grinding, drilling, or by plasma techniques, to be performed on the finished sphere.

A ball and socket joint of properly selected materials will be so effective so as not to require lubrication. Lubricants are progressively depleted in prior art joints requiring lubrication, and thus eventually become prone to failure. By contrast, deterioration of the external surface of the ball, socket, or both by abrasion or by heat build up are both minimized. wear is thus reduced, and longevity of the ball and socket joint is improved.

The principal application of the novel improvement is in the field of prosthetics. Prior art joints have a tendency to wear to the point of requiring eventual replacement. The present invention has the object of eliminating this need for replacement of prosthetic ball and socket joints. Of course, the improved joint may be exploited for other purposes.

Longevity of the joint is more important in prosthetics and possibly other applications than is reduction of friction between ball and socket. To this end, values of smoothness and hardness characteristics are specified and are accorded more weight than are frictional characteristics.

Accordingly, it is a principal object of the invention to provide a ball and socket joint which minimizes wear.

It is another object of the invention that one of the ball and socket be relatively elastic, for conforming to the other member.

It is a further object of the invention to maximize smoothness and hardness of the ball, and to assure that the ball be capable of accepting a hole for receiving a shank.

Still another object of the invention is to enable polishing or smoothing of the ball by a known process typically employed to form spherical objects such as ball bearings.

An additional object of the invention is to form the ball of the ball and socket monolithically from a material having characteristics suitable for the surface of the ball as well as for the interior of the ball.

It is again an object of the invention to eliminate a requirement for lubrication of the ball and socket.

Yet another object of the invention is to increase longevity of joints with the ultimate goal of eliminating necessity of replacing worn prosthetic joints.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENTS

Figure 1:
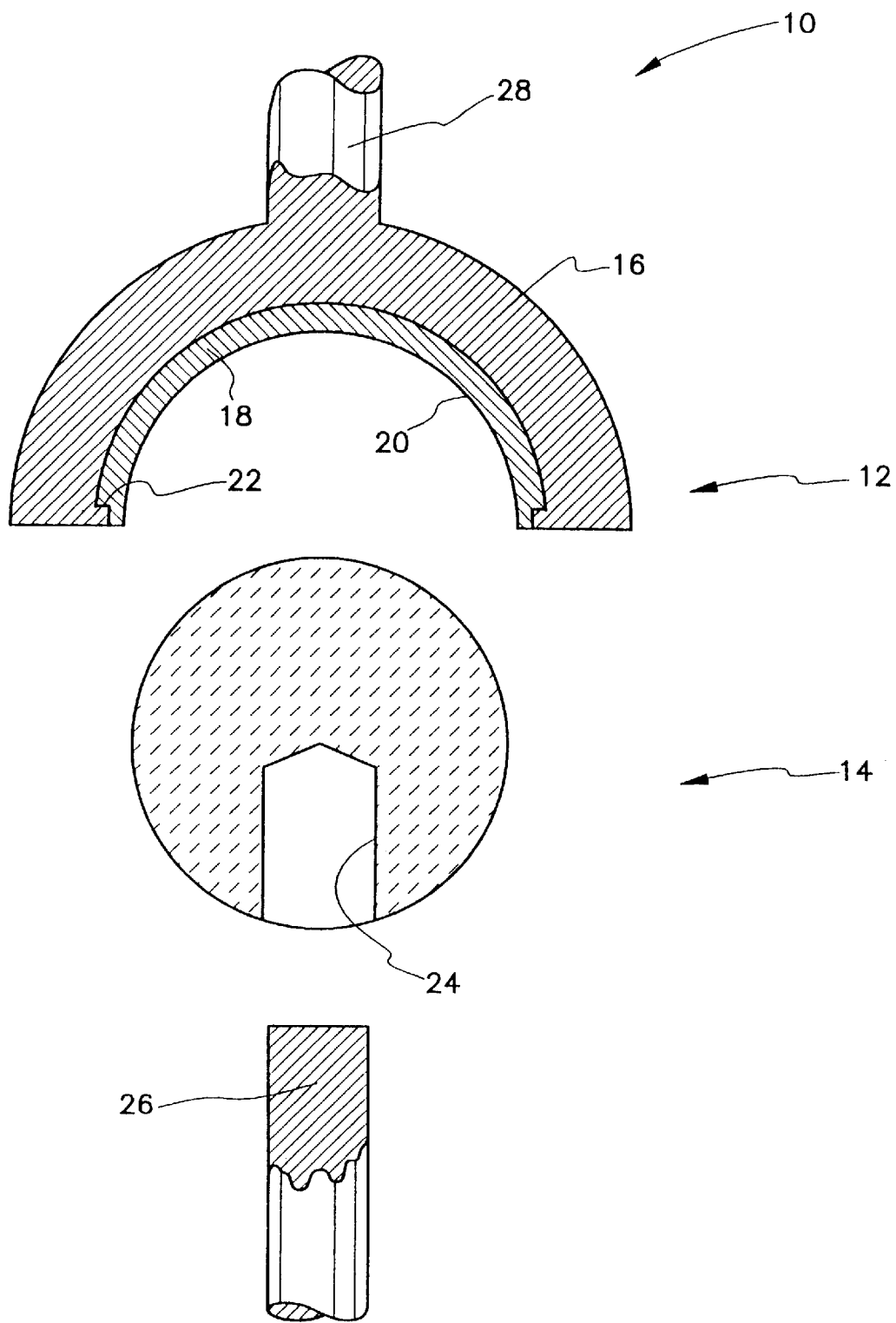
FIG. 1 is an exploded, substantially cross sectional view of the invention.

FIG. 1 shows novel ball and socket joint 10, which comprises a socket 12 and a ball 14 disposed in conventional spherical bearing contact relationship to socket 12. Socket 12 comprises a base 16, or structural supporting member, and a liner 18. Liner 18 is hemispherical, formed from a material selected to provide critical characteristics of the contact surface 20 of socket 12. Surface 20 contacts the outer surface of ball 14. Base 16 has an internal flange 22 for retaining liner 18 within base 16 by mechanical entrapment.

Preferably, ball 14 is formed monolithically from a ceramic material, such as alumina, zirconia, silicon nitride, and silicon carbide. Oxide, nitride, and carbide compounds confer certain important properties upon ball 14 which properties are conducive to long term longevity when placed in service in human endoprosthetic implants. Monolithic construction is preferred since there will be no requirement for coating a ball made from a material lacking in one or more important properties. Also, monolithic construction assures that there is no coating which could degrade, thereby generating large particles of potentially abrasive debris, and possibly subjecting an underlying material to degradation which would not occur if the coating were intact.

These materials are also inert for all practical purposes within the chemical environment of the human body. Ceramics either lack metallic elements which could leach into the body to detrimental effect, or have metallic elements which do not react in conditions encountered in the human body. While these materials are susceptible to chemical attack by very vigorous reagents at elevated temperature and thus are not truly inert, such conditions do not arise in the human body.

Ceramics can both be formed by known processes to be suitably spherical and to accept a preferred microfinish or polish. Isostatic, rolling, or still other methods for forming spheres may be employed to fabricate ball 14. Roundness of the sphere can also be brought to a desirable value when fabricating ball 14 from a ceramic material.

Ceramic also is capable of being finished to a maximum value of 0.3 microinches at the surface. This is a level which minimizes mechanical erosion of the liner.

Ceramics also provide a Mhos hardness value of 11 or greater. it is important that one of the ball 14 and the liner 18 be quite hard and smooth, the other being less hard and somewhat elastic. This important combination of characteristics leads to conformability of surface 20 with ball 14. While it is possible that liner 18 could be formed from the relatively hard and smooth material, it is currently regarded as more feasible to fabricate the ball from such a material. Therefore, ball 14 will be referred to as the relatively harder member, with the understanding that characteristics of ball 14 and socket 12 set forth herein may be reversed.

Hardness of the ball preferably has a Mhos value of eleven or greater, for avoiding or minimizing surface abrasion. However, hardness is preferably below that of diamond, so that final fabrication of ball 14 may include machining by conventional multipoint diamond machining equipment. This is desirable in order to form a bore 24 for accepting a shank 26. Ball and socket joint 10 is intended for connection to two mutually movable members (not shown). Each member requires connection to one of the ball and socket members. This is performed by attachment to a suitable shank. Shank 26 of ball 14 forms one such shank, and shank 28, formed integrally with base 26 of socket 12, provides the other.

Ball 14 has a tensile strength of at least thirty thousand pounds per square inch (hereinafter, psi) to assist in fabrication, and compressive strength of at least two hundred thousand psi, to minimize likelihood of fracture during use.

Ball 14 has a Weibull modulus of value of at least nine, so as to have a clearly defined breaking stress.

It is prefered that ball 14 have sufficient electrical insulative quality to preclude electrolytic reaction with liner 18 or base 16.

Construction and characteristics of socket 12 will now be discussed. Base 16 may be formed from any material which is reasonably strong given bearing loads supporting the human body, and which is chemically compatible with the human body. A metal substance, such as titanium and its alloys, will provide a suitable material for base 16.

Liner 18 may be fabricated from a second metal substance, such as a noble metal and its alloys. Noble metal alloys can usually provide the following requisite characteristics.

Liner 18 has an elastic modulus greater than $10^6$ psi, tensile strength greater than five thousand psi for pure annealed platinum, and greater than thirty thousand psi for most noble metal alloys. Precipitation hardened platinum iridium has a yield strength greater than one hundred thousand psi. For economic reasons, it is possible that other noble metals will be selected.

Liner 18 has a coefficient of friction against the ball material in the range of 0.2 or less.

Potential liner materials include noble metals and their alloys, such as platinum and iridium. Ceramic materials, such as oxides of metals such as zirconium which will satisfy the above conditions, and silicon nitride, silicon carbide, boron carbide, and also an alloptrope of carbon known as glassy carbon may prove suitable.

Certain properties of liner 18 are selected in association with those of ball 14. This requirement overrides mere selection from suggested materials. For example, one of the ball component and the liner component should by hydrophilic, to encourage presence of body fluids. This will assist in lubrication, and in natural flushing of foreign particles from joint 10.

Liner 18 has a Mhos hardness characteristic less than that of ball 14, but greater than that of any body tissue, so that particles of body tissue, such as bone, will not degrade the bearing surfaces.

Of course, liner 18 is chemically inert within the environment of the human body. Base 16 is chemically compatible with the human body.

Figure 2:
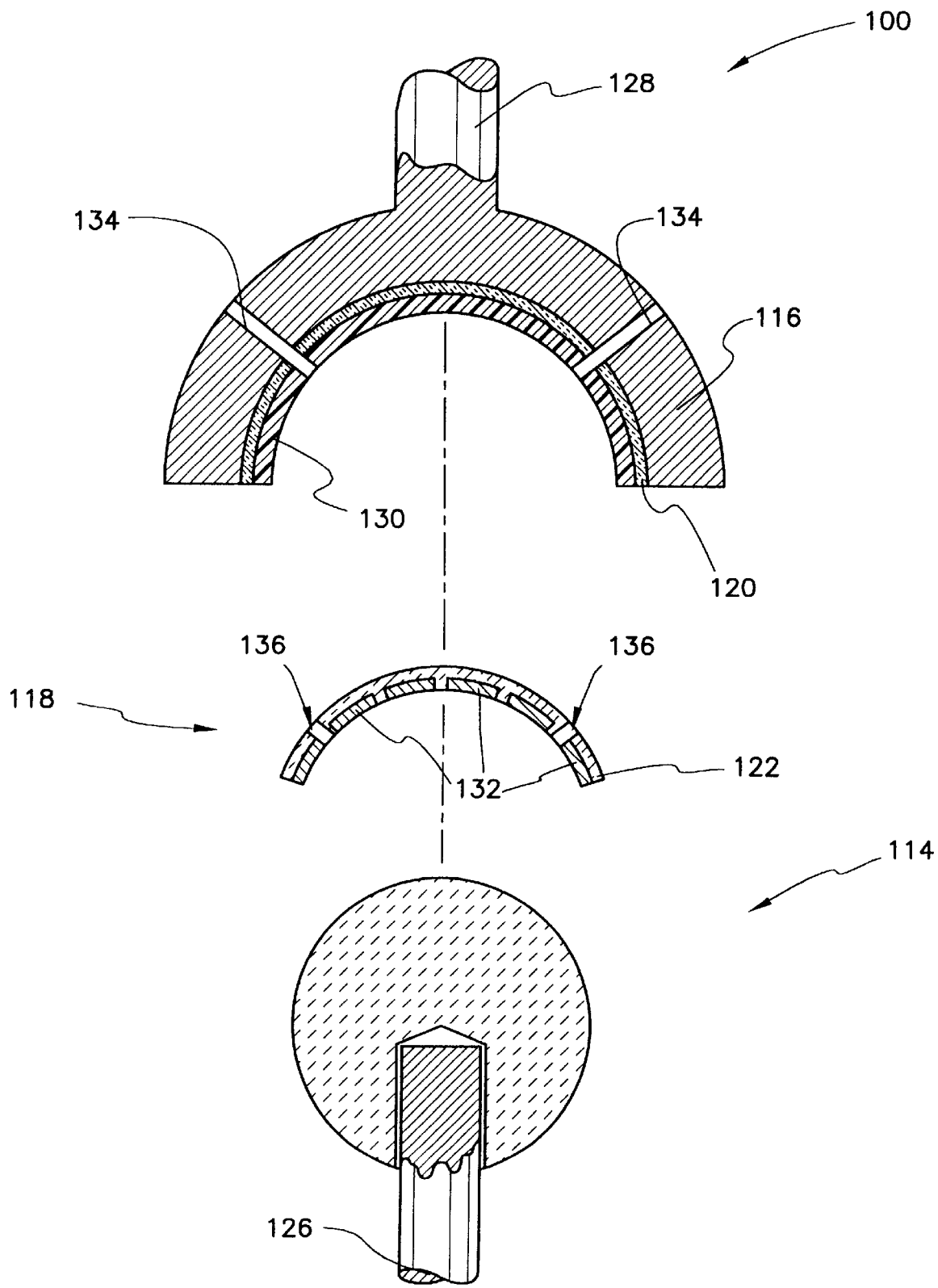
FIG. 2 is an exploded, substantially cross sectional view of an alternative embodiment of the invention.

FIG. 2 shows further features of the invention. In this view, ball and socket joint 100 has socket 112 and ball 114, and respective shanks 128 and 126. However, an electrical insulator 130 is interposed between liner 118 and base 116 of socket 112. Insulator 130 is provided by a sheet of material such as an organic polymer, a layer of adhesive, or any other suitable material. Insulator 120 avoids erosion of base 116 and liner 118 of socket 112 by electrochemical action within the environment of the human body.

It will further be seen that liner 118 is characterized by segmented construction, including segments 132. This construction avoids splitting of liner 118 if a brittle construction material is selected. Liner 118 has an insulator 122 corresponding to insulator 120 of base 116.

Base 116 has passages 134 passing through all components of base 116, including insulators 120 and 130. Liner 118 has corresponding passages 136 which pass through liner 118 and also insulator 122. Passages 134 establish liquid communication between the contact surface of liner 118 and the surrounding body environment. This arrangement enables pressure equilibrium in joint 100 and also enables migration of debris (not shown) from the joint into surrounding body fluids (not shown).

Incorporation of the above characteristics will provide a ball and socket joint suitable for a prosthetic implant for a person and may be expected to provide a service life with repect to wear meeting the average age expectation of a person.

It is to be understood that the present invention is not limited to the embodiments described above, but encompasses any and all embodiments within the scope of the following claims.

I claim:

1. A wear resistant ball and socket joint, comprising:

a socket having a contact surface; and a ball disposed in spherical bearing contact relationship to said contact surface of said socket, one of said ball and said contact surface of said socket having a smoothness finish of magnitude of less than 0.3 microinch, and a hardness characteristic greater than that of the other one of said ball and said contact surface of said socket;

and where one of said ball and said contact surface further has:
- a first Mhos hardness characteristic of at least 11;
- a tensile strength of at least 30,000 psi;
- a compressive strength of at least 200,000 psi;
- a Weibull modulus greater than nine, and further having a hydrophilic characteristic; and where the other of said ball and said contact surface has:
- a second Mhos hardness characteristic less than that of said first Mhos hardness characteristic; whereby said ball and socket joint is suitable for a prosthetic implant for a person and will provide a suitable service life over an average life expectancy.

2. The ball and socket joint according to claim 1, wherein said ball is formed monolithically from a ceramic material.

3. The ball and socket joint according to claim 1, said socket comprising a base and a liner, said contact surface of said socket being disposed upon said liner, said socket having means for retaining said liner by mechanical entrapment.

4. The ball and socket joint according to claim 1, said socket further comprising a base fabricated from a first metal substance and a liner fabricated from a second metal substance, said contact surface of said socket being disposed upon said liner, said socket further comprising an electrical insulator disposed between said liner and said base, whereby erosion of said socket by electrochemical action within the environment of the human body is avoided.

5. The ball and socket joint according to claim 1, said socket comprising a base and a hemispherical liner, said contact surface of said socket being disposed upon said liner, said liner being characterized by segmented construction, whereby splitting of said liner is avoided.

6. The ball and socket joint according to claim 1, said socket comprising a base and a hemispherical liner, said contact surface of said socket being disposed upon said liner, said liner being fabricated from a material having
- a coefficient of friction characteristic less than 0.2 against said ball;
- an elastic modulus characteristic greater than $10^6$ psi; and
- a yield strength characteristic greater than 24,000 psi.

7. The ball and socket joint according to claim 1, said socket comprising a base and a hemispherical liner, said contact surface of said socket being disposed upon said liner, said base and said liner having means defining at least one passage therethrough, for establishing liquid communication between said contact surface and the body environment, whereby migration of debris from said ball and socket joint into body fluids is enabled.

8. A wear resistant ball and socket joint, comprising:
- a socket having a base and a liner, said liner bearing a contact surface, being fabricated from a material having an elastic modulus characteristic greater than $10^6$ psi, a coefficient of friction characteristic less than 0.2 against said ball, and a yield strength characteristic greater than 24,000 psi, said socket having means for retaining said liner by mechanical entrapment; and
- a ball disposed in spherical bearing contact relationship to said contact surface of said socket, said ball
  - being formed monolithically from a ceramic material,
  - having a smoothness finish of magnitude of less than 0.3 microinch,
  - having a first Mhos hardness characteristic of at least 11,
  - having tensile strength of at least 30,000 psi,
  - having compressive strength of at least 200,000 psi, and
  - having a Weibull modulus greater than nine,
- said liner of said socket having a second Mhos hardness characteristic of magnitude greater than that of any body tissue substance of a human body and less than that of said second Mhos hardness characteristic,
- said ball and said socket being fabricated of material chemically inert within the environment of the human body, whereby said ball and socket joint is suitable for a prosthetic implant for a person and may be expected to provide a service life with respect to wear meeting the average age expectation of a person.

9. The ball and socket joint according to claim 8, said base of said socket being fabricated from a first metal substance and said liner being fabricated from a second metal substance, said socket further comprising an electrical insulator disposed between said liner and said base, whereby erosion of said socket by electrochemical action within the environment of the human body is avoided.

10. The ball and socket joint according to claim 8, said liner being characterized by segmented construction, whereby unintended splitting of said liner is avoided.

* * * * *